United States Patent [19]

Saxton

[11] Patent Number: 4,601,897
[45] Date of Patent: Jul. 22, 1986

[54] PRAZOSIN-PIRBUTEROL COMBINATION FOR BRONCHODILATION

[75] Inventor: Craig A. P. D. Saxton, Wilton, Conn.
[73] Assignee: Pfizer Inc., New York, N.Y.
[21] Appl. No.: 795,689
[22] Filed: Nov. 6, 1985
[51] Int. Cl.$^4$ .................. A61K 31/505; A61L 9/04
[52] U.S. Cl. ..................................... 424/45; 514/260
[58] Field of Search ........................ 514/260; 424/45

[56] References Cited

U.S. PATENT DOCUMENTS

| | | | |
|---|---|---|---|
| 3,511,836 | 5/1970 | Hess | 260/256.4 |
| 3,700,681 | 10/1972 | Barth | 260/296 |
| 3,786,160 | 1/1974 | Barth | 424/263 |
| 4,092,315 | 5/1978 | Bianco | 544/291 |
| 4,175,128 | 11/1979 | Taylor | 424/263 |
| 4,271,300 | 6/1981 | Honkanen et al. | 544/291 |
| 4,539,323 | 9/1985 | Mentrup et al. | 514/260 |

OTHER PUBLICATIONS

"Prazosin: Pharmacology, Hypertension and Congestive Heart Failure," Rawlins, Ed., Grune and Stratton, New York, 1981.
Dyson and Mackay, Brit. J. Dis. Chest., 74, 70 (1980).

Primary Examiner—Douglas W. Robinson
Attorney, Agent, or Firm—Charles J. Knuth; Albert E. Frost; Paul D. Thomas

[57] ABSTRACT

A method for relaxing bronchial tissue in mammals, including humans, by use of a combination of prazosin and pirbuterol or their pharmaceutically acceptable acid addition salts.

7 Claims, No Drawings

PRAZOSIN-PIRBUTEROL COMBINATION FOR BRONCHODILATION

BACKGROUND OF THE INVENTION

The invention relates to the use of combinations of the known medicinal agents prazosin, 2-[4-(2-furoyl)-piperazin-1-yl]-4-amino-6,7-dimethoxyquinazoline, and pirbuterol, 2-hydroxymethyl-3-hydroxy-6-(1-hydroxy-2-t-butylaminoethyl))pyridine, for improved bronchodilation in mammals, including humans.

Prazosin and its pharmaceutically acceptable salts were disclosed as antihypertensive agents in U.S. Pat. No. 3,511,836 and U.S. Pat. No. 4,092,315. Pharmacological studies on prazosin hydrochloride were reported by Scriabine et al., *Experientia*, 24, 1150 (1968); by Cohen, *J. Clin. Pharmacol. J. New Drugs*, 10, 408 (1970); Cavero et al. *Life Sci.*, 27, 1525–1540 (1980); and in "Prazosin: Pharmacology, Hypertension and Congestive Heart Failure," Rawlins, Ed., Grune and Stratton, New York, 1981.

The bronchodilator, pirbuterol, was disclosed in U.S. Pat. No. 3,700,681, U.S. Pat. No. 3,786,160. Its use for treatment of congestive heart failure was disclosed in U.S. Pat. No. 4,175,128. Pharmacological studies on pirbuterol were reported by Constantine et al., *J. Pharmacol. Exp. Ther.*, 208, 371 (1979). A comparative study in treating respiratory disease was reported by Dyson and Mackay, *Brit. J. Dis. Chest*, 74, 70 (1980) and its use in treatment of cardiac failure by Colucci et al., *N. Engl. J. Med.*, 305, 185 (1981); Nelson et al. *Eur. Heart J.*, 3, 238 (1982) and Weber et al., *Circulation*, 66, 1262 (1982).

SUMMARY OF THE INVENTION

An enhanced method has now been found for bronchodilation by relaxing bronchial tissue in mammalian subjects including humans, which comprises contacting said tissue with a bronchodilating effective amount of a mixture of prazosin and pirbuterol or the pharmaceutically acceptable acid addition salts thereof, said mixture containing from 10 to 90 parts by weight of prazosin or a pharmaceutically acceptable acid addition salt thereof, and from 90 to 10 parts by weight of pirbuterol or a pharmaceutically acceptable acid addition salt thereof. An especially preferred mixture contains from 20 to 50 parts by weight of prazosin or a pharmaceutically acceptable salt thereof and from 80 to 50 parts by weight of pirbuterol or a pharmaceutically acceptable salt thereof. When said salts of prazosin and/or pirbuterol are employed in the mixtures of the invention, the parts by weight of that component of the mixture are calculated as the free base.

While the mixtures of the invention can be administered to subjects suffering from broncho-constriction by oral or parenteral routes or by inhalation, a peferred method of administration is inhalation by means of an aerosol spray.

The invention further comprises a pharmaceutical composition for aerosol spraying which comprises a pharmaceutically acceptable carrier and a bronchodilating effective amount of the above mixture of prazosin and pirbuterol or said salts.

DETAILED DESCRIPTION OF THE INVENTION

As noted above, the present invention embraces the use of combinations of prazosin and pirbuterol or their pharmaceutically acceptable acid addition salts. Included in such salts are mono- and diacid addition salts of prazosin and pirbuterol. Examples of acids which form such pharmaceutically acceptable salts include hydrochloric, hydrobromic, hydroiodic, nitric, sulfuric, sulfurous, phosphoric, phosphonic, acetic, lactic, citric, tartaric, gluconic, propionic, caproic, lauric and phenylacetic acids. A particularly preferred form of prazosin is the monohydrochloride salt, especially the so-called alpha-form thereof disclosed in U.S. Pat. No. 4,092,315. Particularly preferred forms of pirbuterol are the monoacetate and dihydrochloride salts.

Mixtures of prazosin and pirbuterol containing a wide range of each of these two components or said salts thereof show significantly improved bronchodilating activity in comparison with additive results obtained by use of these ingredients alone. However, a preferred range of prazosin and pirbuterol for such mixtures is from 10 to 90 parts by weight of prazosin and 90 to 10 parts by weight of pirbuterol. An especially preferred mixture is one containing from 20 to 50 parts by weight of prazosin or prazosin hydrochloride and from 80 to 50 parts by weight of pirbuterol or pirbuterol dihydrochloride. In each case when said salts are employed herein, the parts by weight are calculated as the free base.

The above-mentioned mixtures of prazosin and pirbuterol which are useful bronchodilators in mammals, including humans, can be administered as the mixture of the two active ingredients only, but they are ordinarily administered with a pharmaceutically acceptable carrier selected on the basis of the chosen route of administration and standard pharmaceutical practice. For example, they may be combined with various pharmaceutically acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various nontoxic organic solvents. Moreover, the oral pharmaceutical compositions of the mixtures of prazosin and pirbuterol may be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of the standard pharmaceutical practice. For example, where the instant compounds are administered orally in tablet form, excipients such as lactose, sodium citrate, calcium carbonate and dicalcium phosphate may be used. Various disintegrants such as starch, alginic acids, and certain complex silicates, together with lubricating agents such as magnesium stearate, sodium lauryl sulphate and talc, may also be used in producing tablets for the oral adminstration of these compounds. For oral adminstration in capsule form, lactose and high molecular weight polyethylene glycols are among the preferred materials for use as pharmaceutically acceptable carriers. Where aqueous suspensions are to be used for oral adminstration, the active ingredients can be combined with emulsifying or suspending agents. Diluents such as ethanol, propylene glycol, glycerine and their combinations may be employed as well as other materials.

For purposes of parenteral administration and inhalation, solutions or suspensions of the instant combinations prazosin and pirbuterol in sesame or peanut oil or in aqueous propylene glycol solutions can be employed, as well as sterile aqueous solutions of the soluble acid addition salts described herein. These particular solutions of prazosin and pirbuterol are especially suited for intramuscular and subcutaneous injection purposes. The aqueous solutions, including those of the acid addition salts dissolved in pure distilled water, are also useful for intravenous injection purposes provided that the pH of the solution is properly adjusted beforehand. Such solutions shoud also be suitably buffered, if necessary, and the liquid diluent first rendered isotonic with sufficient saline or glucose.

The combination of prazosin and pirbuterol or their pharmaceutically acceptable salts may be administered to subjects suffering from bronchoconstriction by means of inhalators or other devices which permit the acitve compounds to come into direct contact with the constricted respiratory tissues of the subject. When administered by inhalation, the mixture of compounds can comprise (1) a solution or suspension of the two active ingredients in a liquid medium of the type mentioned above for administration via a nebulizer; (2) a suspension or solution of the active ingredients in a liquid propellant such as dichlorodifluoromethane or chlorotrifluoroethane for administration from a pressurized container; or (3) a mixture of the active ingredients and a solid diluent (e.g. lactose) for administration from a powder inhalation device. Compositions suitabe for inhalation by means of a conventional nebulizer will comprise a total of from about 0.1 to about 0.5% of the mixture of active ingredients; and those for use in pressurized containers will comprise a total of from about 0.5 to about 5% of the mixture of active ingredients. Compositions for use as powder inhalants will comprise weight ratios of the total of active ingredients to diluents of from about 1:0.5 to about 1:1.5. When a combination of prazosin and pirbuterol is administered by means of a spray formulated as a solution in an aqueous or nonaqueous solvent, e.g., propellants such as fluorinated hydrocarbons, utilization several times a day is preferred. For such application, a halogenated hydrocarbon propellant having up to 2 carbon atoms is employed. The propellant may be any of the conventional propellants used in aerosol formulations, for example halogenated hydrocarbons of the fluorohydrocarbon or fluorohalohydrocarbon type such as trichloromonofluoromethane, dichlorodifluoromethane, dichlorotetrafluoroethane, monochlorotrifluoromethane, monochlorodifluoromethane, and mixtures of any of these together or with other propellants. Typical of suitable propellants are those disclosed in, for example, U.S. Pat. No. 2,868,691 and sold under the trademark Freon.

It is necessary that the active ingredients, prazosin and pirbuterol or their salts, form a proportion of the composition such that a suitable dosage form will be obtained. Obviously, several dosage unit forms may be administered at about the same time. Although compositions with less than 0.01 percent by weight of total active ingredients might be used in certain instances, it is preferred to use compositions containing not less than 0.01 percent of the active ingredients; otherwise the amount of carrier becomes excessively large. Activity increases with the concentration of the active ingredient mixture. The composition may contain 10, 50, 75, 95 or an even higher percentage by weight of the mixture of active ingredients.

Obviously, the physician will ultimately determine the dosage which will be most suitable for a particular individual, and it will vary with the age, weight and response of the particular patient as well as with the nature and extent of the symptoms and the pharmacodynamic characteristics of the particular agents to be adminstered. Generally, small doses will be administered initially, with a gradual increase in the dosage until the optimum level is determined. It will often be found that when the composition is administered orally, larger quantities of the mixture of active ingredients will be required to produce the same level as produced by a small quantity of the same mixture administered parenterally.

For routine treatment of ambulatory patients suffereing from bronchoconstriction by the instant method, it is generally preferred to administer the instant combination of prazosin and pirbuterol or their pharmaceutically acceptable acid addition salts by the oral route. When said combination of compounds of the invention is administered orally, a daily dosage of from about 2 to 50 mg of the active ingredients is therapeutically effective and dosages of 5 to 30 mg per day administered in increments of 2.5 to 10 mg are preferred.

Parenteral administration, especially by the intravenous route, is recommended for hospitalized patients suffering from acute bronchorestriction. When administered parenterally, an effective dosage is from about 1.0 to 10 mg per day with a preferred range of about 1.0 to 5 mg per day in single or divided doses.

Administration of the prazosin, pirbuterol combinations of the invention by inhalation is indicated for administration in episodes of acute paroxysmal nocturnal dyspnea. When administered in this manner, the effective daily dosage and preferred range are the same as set forth above for parenteral administration.

The above values are illustrative, and there may, of course, be individual cases in which higher or lower dose ranges are merited.

The following examples are provided to illustrate the method of the invention.

EXAMPLE 1

The Effects of Prazosin Hydrochloride and Pirbuterol Hydrochloride Administered Alone and in Combinaton on Histamine-Induced Broncospasm in the Conscious Guinea-Pig Female Dunkin-Hartley guinea-pigs were fasted overnight prior to the experiment but had free access to water except during the periods of exposure to the aerosol. During exposure periods the animals were held in a whole-body plethysmograph# with only the head exposed to the aerosol spray. The pattern of respiration was displayed on a recorder via a low pressure transducer connected to the plethysmograph.

The animals were selected on the basis of the results following an initial exposure to an aerosol of 1.0% histamine acid phosphate in distilled water. * The time to induction of dyspnea of at least 10 seconds duration was recorded during an exposure period not exceeding six minutes. The animals not exhibiting dyspnea lasting for more than 10 seconds during a preliminary three minute exposure period were rejected. Selected groups of 10 guinea-pigs were randomized according to the time taken for dyspnea to occur, so that the group mean perdose values of the various treatment groups were approximately equal.

A device which determines variations in size of a part due to variations in the amount of blood passing through or contained in the part.

Each of the groups of 10 guinea-pigs was exposed to an aerosol treatment, * as shown in Table 1 below, for a period of three minutes. Fifteen minutes ** after exposure to the aerosol treatment containing either vehicle alone, a combination of prazosin hydrochloride/pirbuterol dihydrochloride, prazosin hydrochloride alone, or pirbuterol dihydrochloride alone, the animals were exposed to an aerosol * of 1% histamine acid phosphate and the time to induction of dyspnea was determined. The results are summarized in Table 1.

*In each case the aerosol was generated by a nebulizer operated by compressed air at 20 psi (1.36 bars). Under these conditions it delivered 1.25±0.06 ml of liquid solution as an aerosol spray over a three-minute period.
**The optimum pre-treatment time as determined by preliminary studies.

TABLE 1

Effect of Prazosin HCl and Pirbuterol HCl Alone and in Combination on Histamine-Induced Bronchospasm in the Conscious Guinea-Pig

| | | | Group Mean Time# for Induction of Dyspnea, Seconds ±s.e. | |
|---|---|---|---|---|
| Group No. | Treatment | At Dose, µg/ml | Pre-Dose | 15 min/Post Dose |
| 1 | Vehicle (Distilled Water) | — | 81.2 ± 12.1 | 81.0 ± 8.3 |
| 2 | ↑ | 10 (5 + 5) | 82.8 ± 12.2 | >140.3* ± 26.8 |
| 3 | Prazosin HCl/Pirbuterol HCl | 21.5 (10.75 + 10.75) | 80.0 ± 11.3 | >161.2* ± 36.2 |
| 4 | Combination | 46.4 (23.2 + 23.2) | 79.9 ± 13.3 | >206.3** ± 29.5 |
| 5 | ↓ | 100 (50 + 50) | 77.7 ± 12.1 | >199.3** ± 20.3 |
| 6 | Vehicle | — | 95.4 ± 11.8 | 84.1 ± 9.0 |
| 7 | ↑ | 10 | 89.4 ± 11.8 | 96.1 ± 16.1 |
| 8 | ↑ | 21.5 | 97.2 ± 11.6 | 107.2 ± 11.1 |
| 9 | Prazosin HCl | 46.4 | 92.1 ± 12.8 | 93.0 ± 13.6 |
| 10 | ↓ | 100 | 93.9 ± 12.6 | 139.8 ± 29.7 |
| 11 | Vehicle | — | 65.1 ± 13.6 | 54.5 ± 7.5 |
| 12 | ↑ | 10 | 64.1 ± 12.6 | 56.8 ± 9.5 |
| 13 | Pirbuterol HCl | 21.5 | 64.0 ± 10.8 | >105.4 ± 32.7 |
| 14 | ↓ | 46.4 | 60.2 ± 9.4 | >147.2* ± 38.2 |
| 15 | ↓ | 100 | 60.2 ± 9.0 | >174.9** ± 36.2 |

Significance of difference from the vehicle-treated group using Student's 't' test:
*p<0.05
**p<0.01
Values of >360 seconds have been taken as 360 for calculation of the mean; s.e. = standard error.

Inspection of the data, above, shows that pretreatment with pirbuterol hydrochloride produced a statistically significant dose-related increase in the time required to induce dyspnea following exposure to histamine. Prazosin hydrochloride evoked no statistically significant effect on this time. However, prior exposure to a combination of the two compounds produced a marked, dose-related increase in the induction time. The protective effect of the combination of prazosin hydrochloride and pirbuterol hydrochloride was greater than that obtained by pirbuterol hydrochloride alone.

The synergistic effect of the prazosin HCl/pirbuterol HCl combination over that of the individual components alone was calculated by plotting the increase in group mean time ($\Delta t$) for induction of dyspnea for prazosin HCl alone and pirbuterol HCl alone and extrapolation from the plot the $\Delta t$ value for each of the drugs alone at 5, 10, 75, 23.2 and 50 µg/ml. From these data the additive increase ($\Delta t$ for praxosin HCl alone plus $\Delta t$ for pirbuterol HCl alone) was obtained and the percent synergy at each dose was calculated as follows:

$$\% \text{ Synergy} = 100 \times \frac{(\text{Actual } \Delta t \text{ for combination}) - (\text{Additive } \Delta t)}{(\text{Additive } \Delta t)}$$

The results are summarized in Table 2, below.

TABLE 2

Comparison of the Additive Effects of Prazosin HCl and Pirbuterol HCl Alone with the Actual Effects on Histamine-Induced Bronchospasm in Guinea-Pigs and % Synergy

| Increase in Mean Time (sec.) for Induction of Dyspnea Compared with Vehicle | | | Increase in Mean Time (sec.) for Induction of Dyspnea Compared with Vehicle for 50/50 Combination of Drugs | | | |
|---|---|---|---|---|---|---|
| Dose, µg/ml | Prazosin HCl | Pirbuterol HCl | Dose, µg/ml | Additive Increase | Actual Increase | % Synergy |
| 5.0 | 0.0 | 0.0 | 10 | 0.0 | >69 | ∞ |
| 10.75 | 8.8 | 0.0 | 21.5 | 8.8 | >101 | >1050 |
| 23.2 | 9 | 43 | 46.4 | 52 | >156 | >200 |
| 50.0 | 2 | 90 | 100 | 92 | >156 | >70 |

The results clearly show that a 50/50 combination of prazosin HCl and pirbuterol HCl interact synergistically to afford increased protection against the respiratory effects of histamine compared with the effect of the two individual components administered singly.

EXAMPLE 2

Effects of Prazosin and Pirbuterol Administered Alone and in Combination by Aerosol on Microshock Anaphylaxis by Ovalbumin in the Guinea-Pig Twenty-eight days prior to the experiment, female Dunkin-Hartley guinea-pigs, ten per treatment group, were sensitized with a single intraperitoneal injection of ovalbumin, 10 mg in 1 ml of 0.9% saline solution. The sensitized animals were fasted for 18 hours prior to the test, but water was available and libitum except during the observation period. The left flank of each animal was shaved prior to the test so that the characteristic rippling response could be observed clearly.

The test compounds, prazosin hydrochloride and pirbuterol hydrochloride, were dissolved in distilled water and administered by means of an aerosol operated at 20 pounds per square inch (1.36 bars). The exposure period for each drug treatment was three minutes, * during which time the animals were held in a whole-body plethysmograph. Fifteen minutes after exposure to the test material the animals were subjected to a one-minute exposure to a 1% solution of ovalbumin. They were removed from the exposure chamber and the time taken for a rippling response to be observed on the flank of each animal was recorded. The results are summarized in Tables 3 and 4, below.

*The aerosol was generated by a nebulizer which delivered 1.25±0.06 ml of liquid solution as an aerosol spray over three minutes under these conditions.

TABLE 3

| Group No. | Treatment | At Dose, μg/ml | Group Mean Pre-convulsion Time, Minutes Post Ovalbumin | Group Mean Increase in Pre-convulsion Time from Vehicle, Min. |
|---|---|---|---|---|
| 1# | Vehicle | — | 1.053±0.44 | 0 |
| 2 | Prazosin | 10.0 | 1.059±0.072 | 0.006 |
| 3 | Prazosin | 21.5 | 1.283±0.148 | 0.230 |
| 4 | Prazosin | 46.4 | 1.342±0.136* | 0.289 |
| 5 | Prazosin | 100.0 | 1.308±0.144 | 0.255 |
| 6 | Pirbuterol | 10.0 | 0.904±0.078 | 0 |
| 7 | Pirbuterol | 21.5 | 1.167±0.113 | 0.114 |
| 8 | Pirbuterol | 46.4 | 1.350±0.127* | 0.297 |
| 9 | Pirbuterol | 100.0 | 1.584±0.134*** | 0.531 |
| 10 | Prazosin + Pirbuterol | 5.0 + 5.0 | 1.493±0.127** | 0.44 |
| 11 | Prazosin + Pirbuterol | 10.75 + 10.75 | 1.640±0.205** | 0.587 |
| 12 | Prazosin + Pirbuterol | 23.2 + 23.2 | 1.998±0.227*** | 0.945 |
| 13 | Prazosin + Pirbuterol | 50 + 50 | 2.407±0.359***. | 1.354 |

This group contained 30 guinea-pigs, while all other groups contained only 10 of the animals.
Significance of difference from vehicle treated control animals by Student's 't' test:
*p<0.05
**p<0.01
***p<0.001

In order to express the % synergy of the mixtures prazosin and pirbuterol in increasing the pre-convulsion time in the above test, the above data for each of the two drugs alone were plotted and the respective pre-convulsion time at doses of 5, 10.75, 23.2 and 50 micrograms per milliliter were calculated from the plots. The expected additive effect of prazosin and pirbuterol were then calculated and compared with the pre-convulsion time obtained with the mixtures of the invention containing the same total weight of drug. The results are summarized in Table 4.

TABLE 4

Comparison of the Additive and Actual Effects of a Combination of Prazosin HCl and Pirbuterol HCl on Ovalbumin-Induced Anaphylactic Microshock in the Guinea-Pig

| Increase in Pre-Convulsion Time (min.) Compared with Vehicle | | | Increase in Pre-Convulsion Time with a 50/50 Combination of Prazosin and Pirbuterol | | | |
|---|---|---|---|---|---|---|
| Dose, μg/ml | Prazosin HCl | Pirbuterol HCl | Dose, μg/ml | Additive Increase | Actual Increase | % Synergy |
| 5.0 | 0.004 | 0 | 10.0 | 0.004 | 0.44 | 10,900 |
| 10.75 | 0.02 | 0.005 | 21.5 | 0.025 | 0.587 | 2,250 |
| 23.2 | 0.234 | 0.130 | 46.4 | 0.364 | 0.945 | 160 |
| 50.0 | 0.288 | 0.310 | 100.0 | 0.598 | 1.354 | 125 |

*Percent Synergy = 100 × (Actual-Additive)/Additive

EXAMPLE 3

When the procedures of Examples 1 and 2 are repeated but with mixtures containing prazosin free base or prazosin hydrochloride and pirbuterol dihydrochloride or pirbuterol monoacetate in the weight ratios set forth below, similar results are obtained.

| Component A | Component B | Weight Ratio A:B* |
|---|---|---|
| Prazosin free base | Pirbuterol.2HCl | 10/90 |
| Prazosin.HCl | Pirbuterol.2HCl | 10/90 |
| Prazosin.HCl | Pirbuterol.CH₃COOH | 20/80 |
| Prazosin free base | Pirbuterol.CH₃COOH | 30/70 |
| Prazosin.HCl | Pirbuterol.CH₃COOH | 50/50 |
| Prazosin.HCl | Pirbuterol.2HCl | 55/45 |
| Prazosin.HCl | Pirbuterol.CH₃COOH | 70/30 |
| Prazosin.HCl | Pirbuterol.2HCl | 80/20 |
| Prazosin.HCl | Pirbuterol.HCl | 90/10 |
| Prazosin free base | Pirbuterol free base | 40/60 |
| Prazosin.HCl | Pirbuterol.2HCl | 25/75 |

*The weight is calculated as free base when salts are employed.

Those mixtures containing from 20 to 50 parts by weight of prazosin and from 80 to 50 parts by weight of pirbuterol give especially good results.

EXAMPLE 4

Tablets

A tablet base is prepared by blending the following ingredients in the proportion by weight indicated:
Sucrose U.S.P.: 80.3
Tapioca starch: 13.2
Magnesium stearate: 6.5

Into this tablet base is blended equal weights of 2-hydroxymethyl-3-hydroxy-6-(1-hydroxy-2-t-butylaminoethyl)pyridine dihydrochloride (pirbuterol dihydrochloride) and 2-[4-(2-furoyl)piperazin-1-yl]-4-amino-6,7-dimethoxyquinazoline hydrochloride (prazosin hydrochloride) to provide tablets containing 2.5, 5. 10 and 20 mg of the mixture of active ingredients per tablet. The compositions are pressed into tablets, each weighing 360 mg, by conventional means.

EXAMPLE 5

Capsules

A blend is prepared containing the following ingredients in proportion by weight indicated below:
Calcium carbonate, U.S.P.: 17.6
Dicalcium phosphate: 18.8
Magnesium trisilicate, U.S.P.: 5.2
Lactose, U.S.P.: 5.2
Potato starch 5.2
Magnesium stearate A: 0.8
Magnesium stearate B: 0.35

To this blend is added a sufficient weight of a 50:50 weight mixture of pirbuterol dihydrochloride and prazosin hydrochloride to provide capsules containing 2.5, 5, 10 and 20 mg of the mixture of active ingredients per capsule. The compositions are filled into hard gelatin capsules in the amount of 350 mg per capsule.

EXAMPLE 6

Injectable Preparation

Pirbuterol acetate, 650 g, and 350 g prazosin hydrochloride are intimately mixed and ground with 2,500 g of sodium ascorbate. The ground dry mixture is placed in vials and sterilized with ethylene oxide after which the vials are sterilely stoppered. For intravenous administration, sufficient sterile water is added to the materials in the vials to form a solution containing 1.0 mg of the mixture of active ingredients per milliliter of injectable solution.

EXAMPLE 7

Parenteral Solution

A solution of pirbuterol dihydrochloride and prazosin hydrochloride is prepared with the following composition:

Prazosin.HCl: 3.32 g
Pirbuterol.2HCl: 3.90 g
Magnesium Chloride.6H$_2$O: 12.36 g
Monoethanolamine: 8.85 ml
Propylene glycol: 376.00 g
Distilled water: 94.00 ml The resulting solution has a total concentration of the effective ingredient mixture of 10 mg/ml and is suitable for parenteral administration.

EXAMPLE 8

Suspension

A suspension containing a 20:80 weight mixture of prazosin and pirbuterol, respectively, is prepared having the following composition:

Prazosin.HCl: 5.48 g
Pirbuterol.2HCl: 25.92 g
70% aqueous Sorbitol: 741.29 g
Glycerin, U.S.P.: 185.35 g
Gum acacia (10% solution): 100.00 ml
Polyvinylpyrrolidone: 0.50 g
Distilled water: to make one liter Various sweeteners and flavorants are added to this suspension to improve its palatability. the suspension contains approximately 25 mg of the mixture of effective ingredients per milliliter calculated as the free base.

EXAMPLE 9

Aerosol

An aerosol composition containing equal parts of pirbuterol free base and prazosin free base is prepared as follows:

Prazosin hydrochloride 0.33 g
Pirbuterol acetate 0.38 g
Freon* 115/Freon* 114 (40/60 w/w) 65.29 g
Ethyl alcohol 34.00 g

*Registered Trademark.

The prazosin HCl and pirbuterol acetate are added to the ethyl alcohol and the mixture placed into a plastic coated aerosol bottle. The bottle is charged with the propellant and then sealed with a metering device designed to meter 0.2 gram per dose, equivalent to 0.5 mg of pirbuterol and 0.5 mg of prazosin.

I claim:

1. A method for relaxing bronchial tissue in a mammalian subject which comprises contacting said tissue with a bronchodilating effective amount of a mixture of from 10 to 90 parts by weight of prazosin or a pharmaceutically acceptable acid addition salt thereof and from 90 to 10 parts by weight of pirbuterol or a pharmaceutically acceptable acid addition salt thereof.

2. A method according to claim 1 wherein said mixture contains from 20 to 50 parts by weight of prazosin and from 80 to 50 parts by weight of pirbuterol.

3. A method according to claim 1 wherein prazosin hydrochloride and pirbuterol dihydrochloride are employed.

4. A method according to claim 1 wherein said contacting is effected by means of an aerosol syray.

5. A pharmaceutical composition for aerosol syraying which comprises a pharmaceutically acceptable carrier and a bronchodilating effective amount of a mixture of from 10 to 90 parts by weight of prazosin or a pharmaceutically acceptable acid addition salt thereof and from 90 to 10 parts by weight of pirbuterol or a pharmaceutically acceptable acid addition salt thereof.

6. A pharmaceutical composition according to claim 5 wherein said mixture contains from 20 to 50 parts by weight of prazosin and from 80 to 50 parts by weight of pirbuterol.

7. A pharmaceutical composition according to claim 6 wherein prazosin hydrochloride and pirbuterol dihydrochloride are employed.

* * * * *